United States Patent [19]

Giordano et al.

[11] 4,414,405
[45] Nov. 8, 1983

[54] PROCESS FOR PREPARING ESTERS OF 2-(6'METHOXY-2'NAPHTYL)-PROPIONIC ACID VIA REARRANGEMENT OF NEW KETALS OF 2-HALO-1-(6'-METHOXY-2'-NAPHTYL)-PROPAN-1-ONE AND NEW ESTERS OF 2-(5'-BROMO-6'-METHOXY-2'-NAPHTYL)-PROPIONIC ACID THUS PREPARED

[75] Inventors: Claudio Giordano, Monza; Aldo Belli, Novara; Fulvio Uggeri, Codogno; Giovanni Villa, Monticello Brianza, all of Italy

[73] Assignee: Blaschim S.p.A., Milan, Italy

[21] Appl. No.: 236,513

[22] Filed: Feb. 20, 1981

[30] Foreign Application Priority Data

Feb. 26, 1980 [IT] Italy ............................ 20187 A/80

[51] Int. Cl.³ ............................................. C07C 69/76
[52] U.S. Cl. ................................................... 560/56
[58] Field of Search ........................................ 560/56

[56] References Cited
U.S. PATENT DOCUMENTS 3,607,907  9/1971  Eck ........................................ 560/56
4,107,439  8/1978  Walker et al. ....................... 560/56
4,135,051  1/1979  Walker ................................. 560/56
4,142,054  2/1979  Amin .................................... 560/56

OTHER PUBLICATIONS

McKillop et al., Journ. Amer. Chem. Soc. 95(10), pp. 3340-3343 (1973).

Primary Examiner—Ethel G. Love
Attorney, Agent, or Firm—Stevens, Davis, Miller & Mosher

[57] ABSTRACT

Process for preparing esters of 2-(6'-methoxy-2'-naphtyl)-propionic acid via rearrangement of new ketals of 2-halo-1-(6'-methoxy-2'-naphtyl)-propan-1-one in the presence of a Lewis acid.

The esters thus obtained are useful as intermediate products for preparing Naproxen.

The process involves the preparation of the following new compounds:
ketals of 2-halo-1-(6'-methoxy-2'-naphtyl)-propan-1-one
esters of 2-(5'-bromo-6'-methoxy-2'-naphtyl)-propionic acid
1-(5'-bromo-6'-methoxy-2'-naphtyl)-propan-1-one
2-halo-(5'-bromo-6'-methoxy-2'-naphtyl)-propan-1-one.

1 Claim, No Drawings

PROCESS FOR PREPARING ESTERS OF 2-(6'METHOXY-2'NAPHTYL)-PROPIONIC ACID VIA REARRANGEMENT OF NEW KETALS OF 2-HALO-1-(6'-METHOXY-2'-NAPHTYL)-PROPAN-1-ONE AND NEW ESTERS OF 2-(5'-BROMO-6'-METHOXY-2'-NAPHTYL)-PROPIONIC ACID THUS PREPARED

This invention relates to a new process for preparing esters of 2-(6'-methoxy-2'-naphtyl)-propionic acid via rearrangement of new ketals of 2-halo-1-(6'-methoxy-2'-naphtyl)-propan-1 one in the presence of a Lewis acid; furthermore it relates to some new esters of 2-(5'-bromo-6'-methoxy-2'-naphtyl)-propionic acid.

More particularly the new process of this invention is represented by the following scheme:

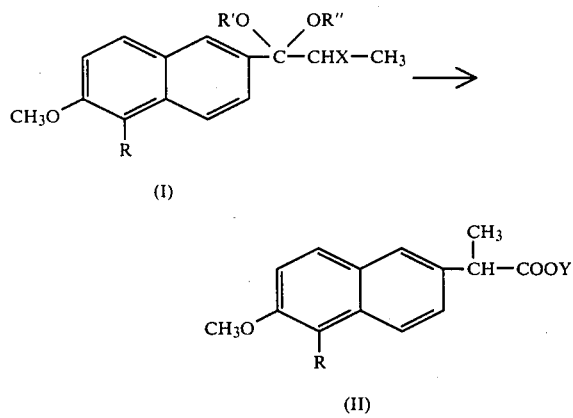

wherein
R is selected from the group comprising an hydrogen and a halogen atom;
R' is selected from the group comprising an alkyl radical having from 1 to 6 carbon atoms and a benzyl radical;
R" is selected from the group comprising an alkyl radical having from 1 to 6 carbon atoms and a benzyl radical;
R' and R", together, are an alkylene radical having 2–6 carbon atoms which, together with the

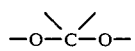

group, forms an heterocyclic ring;
X is a halogen atom;
Y is selected from the group comprising an alkyl radical having from 1 to 6 carbon atoms, a substituted alkyl radical having from 2 to 6 carbon atoms and a benzyl radical.

The esters of general formula II are useful as intermediate products for preparing Naproxen (=D-2-(6'-methoxy-2'-naphtyl)-propionic acid) which is widely used as a drug owing to its antiphlogistic, analgetic and antipyretic activity.

The most part of the known synthetic routes for preparing alpha aryl-alcanoic acids involves the substitution of the aromatic ring with an acyl radical because this substitution may be carried out in high yields and with a high positional selectivity. The subsequent step is consisting in the transformation of the acyl moiety into the alkanoic moiety via Darzen reaction, via a variation of Wittig reaction which comprises the use of methoxycarbenylides instead of carbenylides, via Grignard reaction, via cyanidrine or via reduction to alcohol, subsequent halogenation and treatment with a cyanide or carbon monoxide.

All of the above mentioned procedures present many drawbacks because they involve many steps, the yields are usually low and the reagents are expensive and highly polluting.

In consideration of what above, many efforts have been made to prepare aryl-alkanoic acids via rearrangement of the acyl-derivatives.

A known oxidative rearrangement is the Willgerodt reaction, but it is of industrial value only for preparing the arylacetic acids from the arylmethyl-ketones and it does not allow to achieve good yields because of the many purifications that are needed for eliminating the sulfur-containing by-products.

British Pat. No. 1.535.690 describes a process which comprises (i) the acylation of an aromatic hydrocarbon (ii) the reaction of the ketone thus obtained to prepare the corresponding ketal (iii) the generation of an enol ether from the corresponding ketal (iv) the rearrangement of the enol ether with thallium ions in an organic liquid containing, per equivalent of the enol ether at least one equivalent of a nucleophilic compound. This process suffers the disadvantage that thallium can react with the aromatic moiety to form some by-products.

The alkanoic acids prepared according to this synthetic route contain always traces of thallium as metal and/or as metal-organic product and are potentially dangerous because of the very high toxycity of thallium.

Surprisingly, it has been now found that Lewis acids (J. March-Advanced Organic Chemistry, McGraw-Hill and Kogakusha e. 2^ edt., 236–8; Chem. Rev., 75, No. 1, 1–20) act as catalysts in preparing esters of formula II via rearrangement pathway of ketals of formula I.

In order to obtain the rearrangement, the process is carried out in such a way that the catalyst exerts a good affinity toward the halogen atom and a poor affinity toward the oxygen atom of the ketal group in the alpha-halo-ketal (I).

Meantime, it must be avoided such a condition that catalyst acts as a reducing agent and transforms alpha-halo-ketals (I) into ketals and/or ketones.

Catalysts that may be used according to this invention are the organic salts, such as acetate, propionate, benzoate, trifluoromethane sulphonate, methane sulphonate, etc. as well as the inorganic salts such as chloride, bromide, iodide, sulphate etc. of Copper, Magnesium, Calcium, Zinc, Cadmium, Barium, Mercury, Tin, Antimony, Bismuth, Manganese, Iron, Cobalt, Nickel and Palladium.

A preferred embodiment of this invention contemplates the use of metal halides such as $ZnCl_2$, $CoCl_2$, $ZnBr_2$, $SnCl_2$, $FeCl_2$, $FeCl_3$, $NiBr_2$, $CdCl_2$, $MgCl_2$, $HgCl_2$, $Hg_2Cl_2$, $SbCl_3$, $BaCl_2$, $CaCl_2$, $CuCl$, $CuCl_2$, $MnCl_2$, $SnCl_4$, $BiCl_3$, $PdCl_2$.

The catalyst may be introduced directly into the reaction medium; alternatively, it is formed "in situ".

The catalyst is preferably used in catalytic amount; larger quantities do not afford appreciable advantages.

The rearrangement according to this invention is preferably carried out in the presence of a suitable diluent. Examples of such diluents are the aliphatic halo-hydrocarbons, aliphatic cyclic-hydrocarbons, lower alcohols, aliphatic acids and their esters, aromatic hydrocarbons and aromatic halo-hydrocarbons such as dichloroethane, trichloroethane, chlorobenzene, toluene, methylene chloride, methanol, trimethyl orthoformate, and their mixtures.

The rearrangement contemplated by this invention is conducted at a temperature in the range from about 0° C. to the reflux temperature of the diluent.

Considering that either ketals (I) or esters (II) are stable at high temperature, a preferred embodiment of this invention contemplates the use of high boiling diluents.

The reaction time differs according to the ketal reactivity, the catalyst activity and the reaction temperature; so it is very wide and it is comprised in the range from about ½ hour to about 160 hours.

The meaning of Y in the general formula II is related to the nature of the ketal and/or the diluent.

When R' and R" are an alkyl radical or benzyl radicals and the diluent is not a nucleophilic compound, Y has the same meaning of R' and R".

When an alcohol is used as diluent it may also take part in the esterification and/or transesterification step by forming esters of general formula II wherein Y is the alkyl radical of the alcohol used as diluent. When an alkylene-alpha-halo-ketal (I) is rearranged, then Y (in the ester II) means an halo-alkyl-radical because the halogen atom (X in formula I) replaces one hydroxyl-group or glycol used as precursor whereas the other hydroxyl-group takes part in the formation of the ester group.

Furthermore, scrambling between the anion of the metal salt and the halogen-atom (X in formula I) may take place during the rearrangement step so that the anion of the metal salt may be present as substituent instead of X in the radical Y.

The new halo-ketals (I) are prepared in an easy way and in high yields from the corresponding ketones either (i) by halogenation of the ketone and subsequent ketalization of the thus obtained alpha-halo-ketone or (ii) by ketalization of the ketone and subsequent halogenation of the thus obtained ketal.

The ketalization step may be carried out according to conventional procedures by means of an alcohol in the presence of an acid catalyst and of an ortho ester.

When the ketal is prepared from a glycol, the water which is formed during the reaction is usually removed by azeotropic distillation, for example with benzene, toluene, xylene, trichloroethane, etc.

The introduction of the halogen-atom in alpha position of carbonyl group or of ketal group may be carried out by means of conventional reagents such as sulfuryl chloride, cupric chloride, cupric bromide, N-bromosuccinamide, pyridine or pyrrolidone-perbromide hydrobromide.

The esters of formula II wherein R is a halogen atom are new, consequently they are a further object of this invention.

The halogenation step, the ketalization step and the rearrangement of alpha-halo-ketals of general formula I can be carried out in the same reaction vessel without isolating any intermediate product and in the presence of the same diluent.

The ketones that are used as starting material according to this invention may be prepared by acylating 2-methoxy-naphtalene or 1-halo-2-methoxy-naphtalene according to the Friedel-Crafts reaction.

In addition 2-halo-1-(5'-bromo-6'-methoxy-2'-naphtyl)-propan-1-one may be prepared via conventional bromination of 6-methoxy-2-propionyl-naphtalene or of 2-halo-1-(6'-methoxy-2'-naphtyl)-propan-1-one.

1-(5'-bromo-6'-methoxy-2'-naphtyl)-propan-1-one and 2-halo-(5'-bromo-6'-methoxy-2'-naphtyl)-propan-1-one are new products and therefor they are a further object of this invention.

The removal of the bromine atom from 5-position of the naphtalene ring is carried out according to conventional procedures such as catalytic hydrogenation or reduction by means of Zinc and acetic acid or Zinc and formic acid.

The following specific description is given to enable those skilled in this art to more clearly understand and practice the present invention. It should not be considered as a limitation upon the scope of the invention but merely as being illustrative and representative thereof.

For all of the examples I.R. spectra have been recorded in nujol/NaCl; whereas N.M.R. spectra have been recorded with a 60 MHz spectrometer. The chemical shifts have been expressed in delta [ppm].

EXAMPLE 1

(a)

2-bromo-1,1-dimethoxy-1-(6'-methoxy-2'-naphtyl)-propane (A)

A mixture of 2-bromo-1-(6'-methoxy-2'-naphtyl)-propan-1-one (257 g, 0.877 mol) (prepared according to Bull. Soc. Chim. Fr., 1962, 90), trimethyl orthoformate (271.5 g, 2.56 mol), methanesulfonic acid (1.7 g) and of methanol (700 ml) is kept, under stirring, at 45° C. for 24 h. The reaction mixture is poured, under vigorous stirring, into a saturated sodium carbonate solution and extracted with ethyl ether (2×500 ml).

The combined organic extract is washed with a 2% sodium hydrogen carbonate solution.

Evaporation of the solvent in vacuo leaves 2-bromo-1,1-dimethoxy-1-(6'-methoxy-2'-naphtyl)-propane (290 g, 0.855 mol, yield: 97.5%).

An analytically pure sample is prepared by crystallization from a methanol/trimethyl orthoformate mixture; m.p. 87°–89° C.

I.R.: C=O stretching is absent. No band is present in the 2.5–3.2 microns region.

N.M.R.: (CDCl$_3$/TMS): 1.53 (d, 3H, J=7 Hz); 3.26 (s, 3H); 3.43 (s, 3H); 3.90 (s, 3H); 4.50 (q, 1H, J=7 Hz), 7–7.98 (m, 6H).

(b)

2-chloro-1,1-dimethoxy-1-(6'-methoxy-2'-naphtyl)-propane (B)

A mixture of CuCl$_2$.2H$_2$O (24.56 g, 0.144 mol), lithium chloride (3.06 g, 0.072 mol), 1-(6'-methoxy-2'-naphtyl)-propan-1-one (12.9 g, 0.060 mol) (prepared according to J. Chem. Soc. (C), 1966, 181) and of DMF (40 ml) is kept, under stirring, at 80° C. for 5 h.

The solution is poured into a 3% hydrochloric acid, extracted with ethylether (2×100 ml). The combined organic extract is washed with water, dried on Na$_2$SO$_4$ and the solvent is removed in vacuo. The residue is crystallized from ethanol to give the chloroketone (10.1 g, 0.41 mol, yield: 68%) as analytically pure product, m.p. 76°–78° C.

I.R.: 1680 cm$^{-1}$ (C=O stretching).

N.M.R.: (CDCl$_3$/TMS): 1.72 (d, 3H, J=7 Hz); 3.84 (s, 3H); 5.35 (q, 1H, J=7 Hz); 6.9–8.5 (m, 6H).

A mixture of 2-chloro-1-(6'-methoxy-2'-naphtyl)-propan-1-one (6 g, 24.1 mmol), trimethyl orthoformate (8 g, 75.4 mmol), methanesulfonic acid (0.5 ml, 7.7 mmol) and of methanol (18 ml) is heated at reflux for 30 h. The reaction mixture is cooled to room temperature. The white solid which precipitates is collected by filtration, washed with a mixture of trimethyl orthoformate and methanol and dried; 5.35 g, 18 mmol, yield: 75%; m.p. 92°–94° C.

I.R.: C=O stretching is absent. No band is present in the 2.5–3.2 microns region.

N.M.R.: ($CH_2Cl_2$/TMS): 1.42 (d, 3H, J=7 Hz); 3.3 (s, 3H); 3.45 (s, 3H); 3.95 (s, 3H); 6.85–8.35 (m, 6H).

(c)
2-bromo-1,1-diethoxy-1-(6'-methoxy-2'-naphtyl)-propane (C)

A solution of 2-bromo-1,1-dimethoxy-1-(6'-methoxy-2'-naphtyl)-propane (obtained according to Example 1a) (3.39 g, 10 mmol), triethyl orthoformate (1.34 g, 9 mmol) and of methansulfonic acid (0.098 g, 1 mmol) in ethanol (30 ml) is kept at 46° C. for 2 h.

The reaction mixture is poured, under vigorous stirring, into a saturated sodium carbonate solution and extracted with ethyl ether (2×250 ml). The combined organic extract is washed with a 2% sodium hydrogen carbonate solution and dried on $Na_2CO_3$.

Evaporation of the solvent in vacuo leaves 2-bromo-1,1-diethoxy-1-(6'-methoxy-2'-naphtyl)-propane (3.67 g, 10 mmol, yield: 100%) as oil.

I.R.: C=O stretching is absent. No band is present in the 2.5–3.2 microns region.

N.M.R.: ($CCl_4$/TMS): 1.23 (t, 6H, J=7 Hz); 1.53 (d, 3H, J=7 Hz); 3.43 (q, 4H, J=7 Hz); 3.90 (s, 3H); 4.50 (q, 1H, J=7 Hz); 7.00–8.00 (m, 6H).

(d)
2-(1'-bromoethyl)-2-(6'-methoxy-2'-naphtyl)-1,3-dioxolane (D)

A mixture of 2-bromo-1,1-dimethoxy-1-(6'-methoxy-2'-naphtyl)propane (1 g, 2.94 mmol) (obtained according to Example 1a), trimethyl orthoformate (0.5 ml, 4.7 mmol), $BF_3.Et_2O$ (0.3 ml), and of ethylene glycol (10 ml, 180 mmol) is kept at 50° C. for 3 h. It is cooled to room temperature and poured, under vigorous stirring, into a saturated sodium carbonate solution and extracted with ethyl ether (2×250 ml).

The combined organic extract is washed with a 2% sodium hydrogen carbonate solution.

Evaporation of the solvent in vacuo leaves 2-(1'-bromoethyl)-2-(6'-methoxy-2'-naphtyl)-1,3-dioxolane (0.97 g, 2.82 mmol, yield: 98%).

An analytically pure product is obtained by crystallization from methanol, m.p. 75° C.

I.R.: C=O stretching is absent. No band is present in the 2.5–3.2 microns region.

N.M.R.: ($CDCl_3$/TMS): 1.60 (d, 3H, J=7 Hz); 3.90 (s, 3H); 3.90 (m, 2H); 4.13 (m, 2H); 4.48 (q, 1H, J=7 Hz); 7.04–7.92 (m, 6H).

(e)
2-(1'-bromoethyl)-2-(6'-methoxy-2'-naphtyl)-1,3-dioxane (E)

2-bromo-1-(6'-methoxy-2'-naphtyl)-propan-1-one (10 g, 34 mmol), 1,3-propandiol (10.5 g, 138 mmol), para-toluenesulfonic acid hydrate (1 g, 5.3 mmol) and benzene (50 ml) are refluxed and stirred together for 1 h in a flask beneath a Dean-Stark trap.

The reaction mixture is added dropwise to a well stirred saturated sodium carbonate solution (100 ml), extracted with benzene (2×100 ml). The combined organic solution is washed with a 2% sodium hydrogen carbonate solution, dried ($Na_2CO_3$), filtered and concentrated in vacuo to give 2-(1'-bromoethyl)-2-(6'-methoxy-2'-naphtyl)-1,3-dioxane (11.9 g, 34 mmol, yield: 100%) as oil.

I.R.: C=O stretching is absent. No band is present in the 2.5–3.2 microns region.

N.M.R.: ($CH_2Cl_2$/TMS): 1.20 (m, 2H); 1.68 (d, 3H, J=7 Hz); 3.90 (m, 4H); 3.96 (s, 3H); 4.30 (q, 1H, J=7 Hz); 7.12–7.98 (m, 6H).

(f)
2-(1'-bromoethyl)-2-(6'-methoxy-2'-naphtyl)-4,5-dimethyl-1,3-dioxolane (F)

The preparation is carried out according to the method described in Example 1e.

Reagents: (∓)-2,3-butanediol (10 g, 111 mmol), 2-bromo-1-(6'-methoxy-2'-naphtyl)-propan-1-one (10 g, 34 mmol)

Catalyst: para-toluenesulfonic acid hydrate (1 g, 5.25 mmol)

Solvent: benzene (50 ml)

Reaction time: 7 h

Yield: 12.3 g, 33.7 mmol, 99%, as oil

I.R.: C=O stretching is absent. No band in the 2.5–3.2 microns region.

N.M.R. ($CDCl_3$/TMS): 1.23 (m, 6H); 1.53 (broad d, 3H, J=7 Hz); 3.65 (m, 2H); 3.83 (s, 3H); 4.43 (q, 1H, J=7 Hz); 7.00–8.00 (m, 6H).

(g)
2-(1'-bromo-ethyl)-2-(5'-bromo-6'-methoxy-2'-naphtyl)-1,3-dioxolane (G)

Bromine (7.9 g, 100 mmol) is added, in 30 minutes, to a stirred solution of 2-bromo-1-(6'-methoxy-2'-naphtyl)-propan-1-one (29.3 g, 100 mmol) in chloroform (200 ml), kept at room temperature. The precipitate is filtered and heated at reflux with methanol. The heterogeneous mixture is cooled to room temperature, the insoluble is filtered, washed with methanol and dried: 2-bromo-1-(5'-bromo-6'-methoxy-2'-naphtyl)-propan-1-one (24 g, 64.3 mmol; yield: 64%); m.p. 168°–170° C.

I.R.: 1680 $cm^{-1}$ (C=O stretching).

N.M.R.: ($CDCl_3$/TMS): 1.95 (d, 3H, J=7 Hz); 4.08 (s, 3H); 5.43 (q, 1H, J=7 Hz); 7.23–8.60 (m, 5H).

The 2-bromo-1-(5'-bromo-6'-methoxy-2'-naphtyl)-propan-1-one is converted into 2-(1'-bromoethyl)-2-(5'-bromo-6'-methoxy-2'-naphtyl)-1,3-dioxolane according to the method described in example 1e.

Reagents: ethylene glycol (33.3 g, 0.54 mol), 2-bromo-1-(5'-bromo-6'-methoxy-2'-naphtyl)-propan-1-one (20 g, 0.054 mol)

Catalyst: paratoluenesulfonic acid hydrate (1 g, 5.3 mmol)

Solvent: toluene (25 ml)

Reaction time: 8 h

Yield: 22.1 g, 53 mmol, 99%; m.p. 103°–104° C. (methanol)

I.R.: C=O stretching is absent. No band is present in the 2.5–3.2 microns region.

N.M.R.: ($CDCl_3$/TMS): 1.60 (d, 3H, J=7 Hz); 4.00 (m, 2H); 4.03 (s, 3H); 4.16 (m, 2H); 4.46 (q, 1H, 7 Hz); 7.20–8.36 (m, 5H).

EXAMPLE 2 dl-2-(6'-methoxy-2'-naphtyl)-propionic acid (a) A mixture of 2-bromo-1-(6'-methoxy-2'-naphtyl)-propan-1-one (5.86 g, 20 mmol), trimethyl orthoformate (6 ml), methanesulfonic acid (0.2 ml, 3.1 mmol) and methanol (16 ml) is refluxed under stirring until the ketone is completely transformed into 2-bromo-1,1-dimethoxy-1-(6'-methoxy-2'-naphtyl)-propane.

To the solution thus obtained red cuprous oxide (1.44 g, 10 mmol) is added; the reaction mixture is refluxed under stirring for 24 h.

The suspension is cooled to room temperature and poured into water, the resulting suspension is acidified with hydrochloric acid and extracted with methylene chloride. The organic layer is separated and the solvent is removed under reduced pressure; the residue is dissolved in methanol containing 30% sodium hydroxide aqueous solution. This solution is heated at reflux for 2 hours cooled to room temperature, poured into water and extracted with methylene chloride. The aqueous layer is acidified with diluted hydrochloric acid and extracted with methylene chloride.

The organic extracts are collected and dried over anhydrous sodium sulphate, then the solvent is removed under reduced pressure to give 3.95 g of dl-2-(6'-methoxy-2'-naphtyl)-propionic acid melting at 158°–160° C.

Yield: 86% of the theoretical amount as to the bromo-ketone used as starting product.

(b) A mixture of 2-bromo-1-(6'-methoxy-2'-naphtyl)-propan-1-one (5.86 g, 20 mmol); trimethyl orthoformate (6 ml), p-toluene-sulfonic acid hydrate (0.19 g, 1 mmol) and methanol (16 ml) is refluxed under stirring until the transformation into 2-bromo-1,1-dimethoxy-1-(6'-methoxy-2'-naphtyl)-propane is complete.

To the solution thus obtained red cuprous oxide (0.4 g, 2.8 mmol) is added; the thus obtained mixture is refluxed under stirring for 80 h.

By working up the reaction mixture according to the procedure disclosed in the Example 2a dl-2-(6'-methoxy-2'-naphtyl)-propionic acid (3.6 g) is obtained.

Yield 78% of the theoretical amount as to the bromo-ketone used as starting material.

(c) A mixture of 2-bromo-1,1-dimethoxy-1-(6'-methoxy-2'-naphtyl)-propane (20 mmol), cuprous bromide (10 mmol), trimethyl orthoformate (4 ml) and methanol (16 ml) is refluxed under stirring for 160 h.

By following the procedure disclosed in the Example 2a dl-2-(6'-methoxy-2'-naphtyl)-propionic acid is obtained whereas the cuprous salt is recovered quantitatively and it is suitable for being recycled.

Yield, 70% of the theoretical amount as to the bromo-ketone used as starting material.

(d) A mixture of 2-bromo-1-(6'-methoxy-2'-naphtyl)-propan-1-one (2.93 g, 10 mmol), trimethyl orthoformate (3 ml), methanesulfonic acid (0.1 ml; 1.35 mmol) and methanol (8 ml) is refluxed under stirring until the transformation into 2-bromo-1,1-dimethoxy-1-(6'-methoxy-2'-naphtyl)-propane is complete.

To the solution thus obtained cupric benzoate (3.3 g, 11 mmol) and copper powder (0.7 g, 11 mmol) are added; the thus obtained mixture is refluxed under stirring for 20 h.

By working up the reaction mixture according to the procedure disclosed in the Example 2a dl-2-(6'-methoxy-2'-naphtyl)-propionic acid (0.95 g, 4.1 mmol) is obtained.

Yield, 41% of the theoretical amount as to the bromo-ketone used as starting material.

Analogous results have been obtained by using catalytic amounts of the catalyst.

(e) A mixture of anhydrous cupric acetate (0.9 g, 5 mmol), copper powder (0.32 g, 5 mmol), methanesulfonic acid (0.7 mmol) and acetic anhydride (5 ml) is stirred for 1 h at 65° C.

To the mixture cooled to room temperature 2-bromo-1,1-dimethoxy-1-(6'-methoxy-2'-naphtyl)-propane (1.7 g, 5 mmol) is added.

The thus obtained mixture is heated to 65° C. and maintained at this temperature, under stirring. for 20 h.

By working up the reaction mixture according to the procedure disclosed in the Example 2a dl-2-(6'-methoxy-2'-naphtyl)-propionic acid (0.67 g) is obtained.

Yield, 58% of the theoretical amount as to the bromo-ketone used as starting material.

Analogous results have been obtained by using catalytic amounts of the catalyst.

(f) A mixture of 2-bromo-1-(6'-methoxy-2'-naphtyl)-propan-1-one (5.86 g, 20 mmol), trimethyl orthoformate (6 ml), 96% sulfuric acid (0.51 ml, 5 mmol) and of methanol (20 ml) is refluxed under stirring until the transformation into 2-bromo-1,1-dimethoxy-1-(6'-methoxy-2'-naphtyl)-propane is complete.

To the solution thus obtained red cuprous oxide (2.88 g, 20 mmol) is added; the thus obtained mixture is then refluxed under stirring for 16 h.

By working up the reaction mixture according to the procedure disclosed in the Example 2a dl-2-(6'-methoxy-2'-naphtyl)-propionic acid (3.85 g) is obtained.

Yield, 84% of the theoretical amount as to the bromo-ketone.

Analogous results have been obtained by using catalytic amounts of the catalyst.

(g) A mixture of 2-bromo-1-(6'-methoxy-2'-naphtyl)-propan-1-one (2.93 g, 10 mmol), triethyl orthoformate (2 ml), methanesulfonic acid (0.2 ml, 2.7 mmol) and of ethanol (8 ml) is refluxed, under stirring, for 48 h.

The solution of the ethyl-ketal thus obtained is cooled to 65° C. and red cuprous oxide (2.88 g, 20 mmol) added; the reaction mixture is then kept at 65° C. under stirring for 8 h.

By working up the reaction mixture according to the procedure disclosed in the Example 2a dl 2-(6'-methoxy-2'-naphtyl)propionic acid (0.2 g, 0.87 mmol) is obtained.

Yield 87% of the theoretical amount as to the bromo-ketone.

Analogous results have been obtained by using catalytic amounts of the catalyst.

(h) A mixture of copper powder (0.65 g, 10.2 mmol), methanesulfonic acid (0.04 ml, 0.6 mmol), trimethyl orthoformate (1 ml) and of methanol (4 ml) is heated at reflux, under nitrogen, for 30 minutes.

2-bromo-1,1-dimethoxy-1-(6'-methoxy-2'-naphtyl)-propionic acid (1.7 g, 5 mmol) is added to the reaction mixture, cooled to room temperature.

The reaction mixture is heated at reflux for 40 h, under stirring and under nitrogen.

dl-2-(6'-methoxy-2'-naphtyl)-propionic acid (0.35 g, 1.5 mmol; yield 30%) (m.p. 158°–160° C.) is isolated by working up the reaction mixture as described in Example 2a.

EXAMPLE 3

Methyl dl-2-(6'-methoxy-2'-naphtyl)-propionate

A solution is prepared by adding 2-bromo-1,1-dimethoxy-1-(6'-methoxy-2'-naphtyl)-propane (339 g, 1 mol) prepared according to the procedure disclosed in the Example 2a, to 1000 ml of methylene chloride. To this solution $ZnCl_2$ (19.8 g, 0.17 mol) is added under stirring, at 20° C.

The suspension is kept under stirring, at 20° C. for 10 h. The suspension is then washed with 10% hydrochloric acid (2×250 ml) and the solvent is removed by distillation under reduced pressure. The yield of the methyl dl-2-(6'-methoxy-2'-naphtyl)-propionate is 215 g (yield, 88%).

EXAMPLE 4

2-bromoethyl-ester of dl 2-(5'-bromo-6'-methoxy-2'-naphtyl)-propionic acid

A mixture of 2-(1'-bromoethyl)-2-(5'-bromo-6'-methoxy-2'-naphtyl)-1,3-dioxolane (2 g, 4.8 mmol), $ZnBr_2$ (0.1 g, 0.45 mmol) and of toluene (5 ml) is heated at reflux for 5 h. The reaction mixture is cooled, poured into 3% hydrochloric acid (50 ml) and extracted with toluene (2×50 ml). The combined organic extract is washed with water, dried ($Na_2SO_4$) and filtered.

Evaporation of the solvent under reduced pressure gives 2-bromo-ethyl ester of 2-(5'-bromo-6'-methoxy-2'-naphtyl)-propionic acid (1.98 g, 4.75 mmol; yield 98%).

An analytically pure sample is obtained by crystallization from methanol; m.p. 78°–79° C.

I.R.: 1730 cm$^{-1}$ (C=O stretching absent).
N.M.R.: (CDCl$_3$/TMS): 1.57 (d, 3H, J=7 Hz); 3.40 (t, 2H, J=7 Hz); 3.94 (s, 3H); 3.94 (q, 1H, 7 Hz); 4.37 (t, 2H, J=6 Hz); 7.06–8.34 (m, 5H).

In an analogous manner several alpha-halo-ketals have been rearranged in the presence of several catalysts, in several solvent and at different temperatures.

The results that have been obtained are summarized in the following table wherein:

- the alpha-halo-ketals are indicated with the capital letter which follows their chemical names in Example 1;
- the solvents are indicated as M (methanol), DCE (dichloroethane), MEC (methylene chloride), TMOF (trimethyl orthoformate), TOL (toluene), TCE (tetrachloroethane), CB (chlorobenzene);
- yields as to the ketal used as starting material are based on the propionic acid obtained via hydrolisis of crude esters.

TABLE

| Catalyst (mmoles) | Ketal (mmoles) | Diluent (ml) | Reaction time (h) | T (C.°) | Yield |
|---|---|---|---|---|---|
| BaCl$_2$ (1.6) | D (5) | TCE (5) | 5 | 145 | 95 |
| BiCl$_3$ (5) | A (5) | MEC (10) | 24 | 15 | 35 |
| CaCl$_2$ (1.6) | D (5) | TCE (5) | 24 | 145 | 15 |
| CaCl$_2$ (1.6) | D (5) | TCE (5) | 7 | 145 | 95 |
| CoCl$_2$ (15) | A (5) | M (5) + TMOF (1) | 120 | 60 | 45 |
| CoCl$_2$ (10) | A (10) | DCE (10) | 72 | 80 | 40 |
| CoCl$_2$ (1.5) | D (4.5) | TOL (4) | 10 | 110 | 98 |
| CuCl$_2$ (5) | A (5) | DCE (10) | 24 | 60 | 10 |
| CuCl$_2$ (15) | A (5) | M (5) + TMOF (1) | 120 | 60 | 30 |
| FeCl$_2$ (1.6) | D (5) | TOL (5) | 10 | 110 | 80 |
| FeCl$_3$ (6) | A (6) | MEC (6) | 14 | 15 | 78 |
| FeCl$_3$ (57) | A (57) | MEC (57) | 5 | 0 | 77 |
| Hg$_2$Cl$_2$ (1.6) | D (5) | TCE (5) | 6 | 145 | 92 |
| HgCl$_2$ (1.6) | D (5) | TOL (5) | 3 | 110 | 87 |
| MgCl$_2$ (1.6) | D (5) | TCE (5) | 22 | 145 | 35 |
| MnCl$_2$ (15) | A (5) | M (5) + TMOF (1) | 120 | 60 | 30 |
| NiBr$_2$ (1.6) | D (5) | TCE (5) | 21 | 145 | 28 |
| PdCl$_2$ (15) | A (5) | M (5) + TMOF (1) | 3 | 60 | 92 |
| SbCl$_3$ (1.6) | D (5) | TCE (5) | 3 | 145 | 96 |
| SnCl$_2$ (1.6) | D (5) | TOL (5) | 12 | 110 | 95 |
| SnCl$_4$ (5) | A (5) | MEC (10) | 24 | 20 | 20 |
| ZnBr$_2$ (3) | D (15) | TOL (30) | 4 | 110 | 98 |
| ZnBr$_2$ (1.3) | D (5) | CB (5) | 0.5 | 132 | 97 |
| ZnBr$_2$ (0.45) | G (4.8) | TOL (5) | 5.5 | 110 | 98 |
| ZnCl$_2$ (22) | A (155) | MEC (150) | 4 | 30 | 84 |
| ZnCl$_2$ (109) | A (750) | MEC (750) | 12 | 20 | 86 |
| ZnCl$_2$ (5) | A (50) | MEC (50) | 16 | 15 | 96 |
| ZnCl$_2$ (73) | A (500) | TOL (700) | 6 | 60 | 80 |
| ZnCl$_2$ (170) | A (1000) | MEC (1000) | 10 | 20 | 88 |
| ZnCl$_2$ (11) | B (10) | MEC (15) | 8 | 45 | 13 |
| ZnCl$_2$ (2.5) | C (10) | MEC (17) | 24 | 15 | 40 |
| ZnCl$_2$ (8.4) | D (68) | TOL (200) | 6 | 110 | 96 |
| ZnCl$_2$ (3) | D (3) | MEC (6) | 24 | 15 | 10 |
| ZnCl$_2$ (3) | E (9) | TOL (10) | 16 | 90 | 90 |
| ZnCl$_2$ (4.5) | F (13.7) | TOL (15) | 14 | 90 | 80 |
| ZnCl$_2$ (7) | F (7) | MEC (20) | 24 | 45 | 30 |
| ZnCl$_2$ (1.6) | G (5) | TOL (5) | 2 | 110 | 90 |
| Zn (OAc)$_2$ (0.25) | D (5) | TOL (5) | 2 | 110 | 98 |

We claim:
1. Process for preparing a compound having the formula:

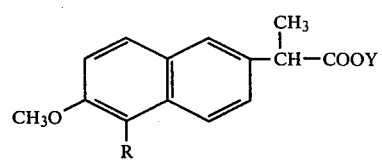

wherein

R is selected from the group consisting of a hydrogen and a bromine atom; and

Y is selected from the group consisting of an alkyl radical having from 1 to 6 carbon atoms, a haloalkyl radical having from 2 to 6 carbon atoms, and a benzyl radical;

which comprises the rearrangement of a compound having the formula:

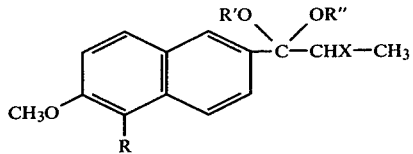

wherein

R has the above mentioned meaning;

R' is selected from the group consisting of an alkyl radical having from 1 to 6 carbon atoms and a benzyl radical;

R" is selected from the group consisting of an alkyl radical having from 1 to 6 carbon atoms and a benzyl radical; or R' and R", together, are an alkylene radical having from 2–6 carbon atoms which, together with the

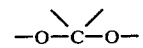

group, forms a heterocyclic ring; and

X is a halogen atom in the presence of a catalytic amount of a Lewis acid.

* * * * *

UNITED STATES PATENT AND TRADEMARK OFFICE
CERTIFICATE OF CORRECTION

PATENT NO. : 4,414,405

DATED : November 8, 1983

INVENTOR(S) : GIORDANO, et al.

It is certified that error appears in the above-identified patent and that said Letters Patent is hereby corrected as shown below:

In the heading of the patent please amend the priority information to read as follows:

--[30] FOREIGN APPLICATION PRIORITY DATA

February 26, 1980 Italy.....20187 A/80;

August 7, 1980 Italy......24045 A/80.--

Signed and Sealed this

Twenty-seventh Day of May 1986

[SEAL]

Attest:

DONALD J. QUIGG

Attesting Officer

Commissioner of Patents and Trademarks